(12) United States Patent
Leana et al.

(10) Patent No.: US 8,722,373 B2
(45) Date of Patent: *May 13, 2014

(54) **CONTAMINANT CONTROL IN *ZYMOMONAS* FERMENTATION USING VIRGINIAMYCIN**

(71) Applicant: E I du Pont de Nemours and Company, Wilmington, DE (US)

(72) Inventors: Maria C Leana, Hockessin, DE (US); Brian G Lefebvre, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/101,375

(22) Filed: Dec. 10, 2013

(65) Prior Publication Data

US 2014/0099689 A1    Apr. 10, 2014

Related U.S. Application Data

(62) Division of application No. 13/524,255, filed on Jun. 15, 2012.

(51) Int. Cl.
    *C12P 7/06*     (2006.01)
    *C12P 1/04*     (2006.01)

(52) U.S. Cl.
    USPC .......................................... 435/161; 435/170

(58) Field of Classification Search
    USPC .................................................. 426/161, 170
    See application file for complete search history.

(56) References Cited

U.S. PATENT DOCUMENTS

| | | | |
|---|---|---|---|
| 5,514,583 | A | 5/1996 | Picataggio et al. |
| 5,712,133 | A | 1/1998 | Picataggio et al. |
| 5,843,760 | A | 12/1998 | Zhang et al. |
| 6,566,107 | B1 | 5/2003 | Zhang |
| 7,629,156 | B2 | 12/2009 | Viitanen et al. |
| 7,741,119 | B2 | 6/2010 | Viitanen et al. |
| 7,897,396 | B2 | 3/2011 | Caimi et al. |
| 7,989,206 | B2 | 8/2011 | Viitanen et al. |
| 7,998,722 | B2 | 8/2011 | Viitanen et al. |
| 2003/0016227 | A1 | 1/2003 | Matthies |
| 2009/0042276 | A1 | 2/2009 | Maye |
| 2011/0043408 | A1 | 2/2011 | Shi et al. |
| 2011/0318803 | A1 | 12/2011 | Hitz et al. |
| 2012/0156746 | A1 | 6/2012 | Caimi et al. |
| 2012/0208255 | A1 | 8/2012 | Anderson et al. |

FOREIGN PATENT DOCUMENTS

| | | |
|---|---|---|
| WO | 9528476 A1 | 10/1995 |
| WO | 2007145857 A1 | 12/2007 |
| WO | 2010093765 A1 | 8/2010 |

OTHER PUBLICATIONS

Agrawal, Renu et al., Role of Antimicrobial Agents in Simultaneous Saccharification and Fermentation of Paddy Malt Mash to Ethanol by Mixed Cultures of *Saccharomyces cervisiae* PHO3 and *Zymomonas mobilis* ZM4, Biotechnology Letters, Jun. 1996, pp. 673-678, vol. 18, No. 6.
Bischoff, Kenneth M. et al., Modeling Bacterial Contamination of Fuel Ethanol Fermentation, Biotechnology and Bioengineering, May 1, 2009, pp. 117-122, vol. 103, No. 1.
Day, W. H. et al., Antibiotics as Contamination-Control Agents in Grain Alcohol Fermentations, Agricultural and Food Chemistry, Mar. 3, 1954, pp. 252-258, vol. 2, No. 5.
Hynes, S. H. et al., Use of virginiamycin to control the growth of lactic acid bacteria during alcohol fermentation, Journal of Industrial Microbiology & Biotechnology, 1997, pp. 284-291, vol. 18.
Mohagheghi, Ali et al., Performance of a newly developed integrant of *Zymomonas mobilis* for ethanol production on corn stover hydrolysate, Biotechnology Letters, 2004, pp. 321-325, vol. 26.
Swings, J. et al., The Biology of *Zymomonas*, Bacteriological Reviews, Mar. 1977, pp. 1-46, vol. 41, No. 1.
Walia, S. K. et al., Self-Transmissible Plasmid in *Zymomonas mobilis* Carrying Antibiotc Resistance, Jan. 1984, pp. 198-200, vol. 47, No. 1.
Feldmann, Sigrun D. et al., Pentose metabolism in *Zymomonas mobilis* wild-type and recombinant strains, Applied Microbiology and Biotechnology, 1992, pp. 354-361, vol. 38.
Zhang, Min et al., Metabolic Engineering of a Pentose Metabolism Pathway in Ethanologenic *Zymomonas mobilis*, Science, Jan. 13, 1995, pp. 240-243, vol. 267.
Grote, W. et al., The Susceptibility of Contamination of a *Zymomonas mobilis* Process for Ethanol Production, Journal of Fermentation Technology, 1985, pp. 287-290, vol. 63, No. 3.
Agrawal, Renu et al., Fermentation of Paddy Malt Mash to Ethanol by Mixed Cultures of *Saccharomyces cerevisiae* and *Zymomonas mobilis* ZM4 with Penicillin G, Journal of Fermentation and Bioengineering, 1994, pp. 218-220, vol. 77, No. 2.
International Search Report dated Aug. 29, 2013, International Application No. PCT/US2013/044909.

*Primary Examiner* — Maryam Monshipouri

(57) ABSTRACT

Contamination was controlled in fermentations using *Zymomonas mobilis* as the biocatalyst, without negative impact on fermentation production, by the addition of virginiamycin. The effective concentration of virginiamycin was found to be dependent upon the type of fermentation medium used.

7 Claims, 11 Drawing Sheets

CONTAMINANT CONTROL IN *ZYMOMONAS* FERMENTATION USING VIRGINIAMYCIN

This application is a divisional of application Ser. No. 13/524,255 filed Jun. 15, 2012, pending.

FIELD OF THE INVENTION

The invention relates to the fields of microbiology and fermentation. More specifically, methods were developed for controlling contaminants of fermentations when *Zymomonas* is used as the biocatalyst.

BACKGROUND OF THE INVENTION

Fuel ethanol produced from renewable resources is one of the long-term solutions to global fossil fuel shortages, rising energy costs, and global warming effects related to increased atmospheric carbon dioxide. Fuel ethanol from renewable resources is produced by fermentation of sugars using a biocatalyst. Currently yeast is the biocatalyst most widely used for ethanol production. Fermentable sugars are most typically obtained from processed biomaterials including corn grain, sugar beets, and sugar cane. An alternative abundant biomaterial sugar source is cellulosic or lignocellulosic biomass. Methods are being developed for processing of cellulosic and lignocellulosic biomass to produce fermentable sugars using physical, chemical, and/or enzymatic treatments.

It is difficult to maintain sterility in a large scale fermentation process, particularly when biomaterial is used as as a carbohydrate source. Large scale fermentation processes are typically contaminated with bacteria that may come from the processed biomaterial, equipment, process water or other sources. Typically contaminating bacteria are lactic acid bacteria (LAB) such as *Lactobacillus* species. Contaminating bacteria reduce fermentation product yield by utilizing sugars and reducing effectiveness of the primary product biocatalyst. Contaminating bacteria produce undesired products such as acetic and lactic acid which increase stress conditions in a culture leading to poorer growth of the biocatalyst and/or lower production of the biocatalyst product.

Contaminating bacteria, predominantly lactic acid bacteria, have been a problem in fermentations that use yeast as the biocatalyst, typically with mash or molasses used as the carbohydrate source for ethanol production for either fuel or brewing. Due to differential sensitivities of yeast and contaminating bacteria to some antimicrobials, a number of antimicrobials can be used to control bacteria in yeast fermentations. Antimicrobials successfully used in yeast fermentations to control LAB contamination include penicillin (Day et al. (1954) Agricultural and Food Chemistry 2:252-258), virginiamycin (Hynes et al. (1997) J. of Industrial Microbiology & Biotechnology 18:284-291; Bischoff et al. (2009) Biotechnology and Bioengineering 103:117-122; WO2007145857), hop acids (US20090042276), FermaSure™, as well as erythromycin, tylosin, and tetracycline.

*Zymomonas* is being developed as an effective biocatalyst for producing ethanol by engineering strain improvements including utilization of xylose and arabinose in addition to glucose, and inactivating competing metabolic pathways. In addition, *Zymomonas* has been adapted for use in hydrolysate fermentation medium by increasing tolerance to inhibitors present in cellulosic biomass hydrolysate. However, using *Zymomonas* as a biocatalyst for ethanol fermentation presents additional challenges in contamination control since this biocatalyst is a bacterium, as are the predominant contaminants.

Concentrations of many antibiotics that are safe to use with yeast are inhibitory to growth of *Zymomonas mobilis* strain ZM4, including tetracycline, kanamycin, polymixin and streptomycin (Agrawan and Basappa, Biotechnology Letters (1996) 18:673-678). Only penicillin G was shown to be safe for use with *Zymomonas*. Benzyl penicillin was successfully used to control bacterial contamination in batch *Zymomonas mobilis* fermentation for ethanol production (Grote and Rogers, Journal of Fermentation Technology (1985) 63:287-290). In another review *Zymomonas* was reported as a contaminant of cider and beer, and strains of *Zymomonas* with resistance to typically used levels of some antibiotics including kanamycin, polymyxin, and sreptomycin were found (Swings and De Ley, Bacteriological Reviews (1977) 41:1-46). Differences among strains may be related to the encoding of resistance on plasmids, as was found for streptomycin, kanamycin, and gentamicin in *Z. mobilis* strain CP4 (Walia et al. (1984) Applied and Environmental Microbiology 47:198-200).

There remains a need for methods to control bacterial contaminants in fermentations that use a bacterial *Zymomonas* biocatalyst that has been developed for ethanol production.

SUMMARY OF THE INVENTION

The invention provides fermentation broth compositions and methods for controlling bacterial contamination in media where *Zymomonas* is the biocatalyst.

Accordingly, the invention provides a fermentation broth composition comprising:
  a) fermentation medium;
  b) virginiamycin; and
  d) a growing population of *Zymomonas* cells.

In another aspect the invention provides a method for controlling bacterial contamination in a fermentation using a *Zymomonas* biocatalyst comprising:
  a) providing a fermentation medium;
  b) adding virginiamycin to the fermentation medium;
  c) adding to the fermentation medium an inoculum of *Zymomonas* cells, thereby producing a fermentation broth; and
  d) maintaining the fermentation broth under conditions suitable for growth of the *Zymomonas* cells;
wherein steps b) and c) may be performed in either order or concurrently and wherein bacterial contamination is controlled.

In one embodiment ethanol is produced in the fermentation broth of this method.

In yet another aspect the invention provides a method for producing ethanol comprising:
  a) providing a fermentation medium;
  b) adding to the fermentation medium an inoculum of *Zymomonas* cells grown in the presence of virginiamycin producing a fermentation broth; and
  c) maintaining the fermentation broth under conditions suitable for growth of the *Zymomonas* cells and production of ethanol by the *Zymomonas* cells;
wherein ethanol is produced.

In yet another aspect the invention provides a method for improving growth of *Zymomonas* cells comprising growing *Zymomonas* cells in fermentation medium comprising virginiamycin.

DETAILED DESCRIPTION

Figure 1:
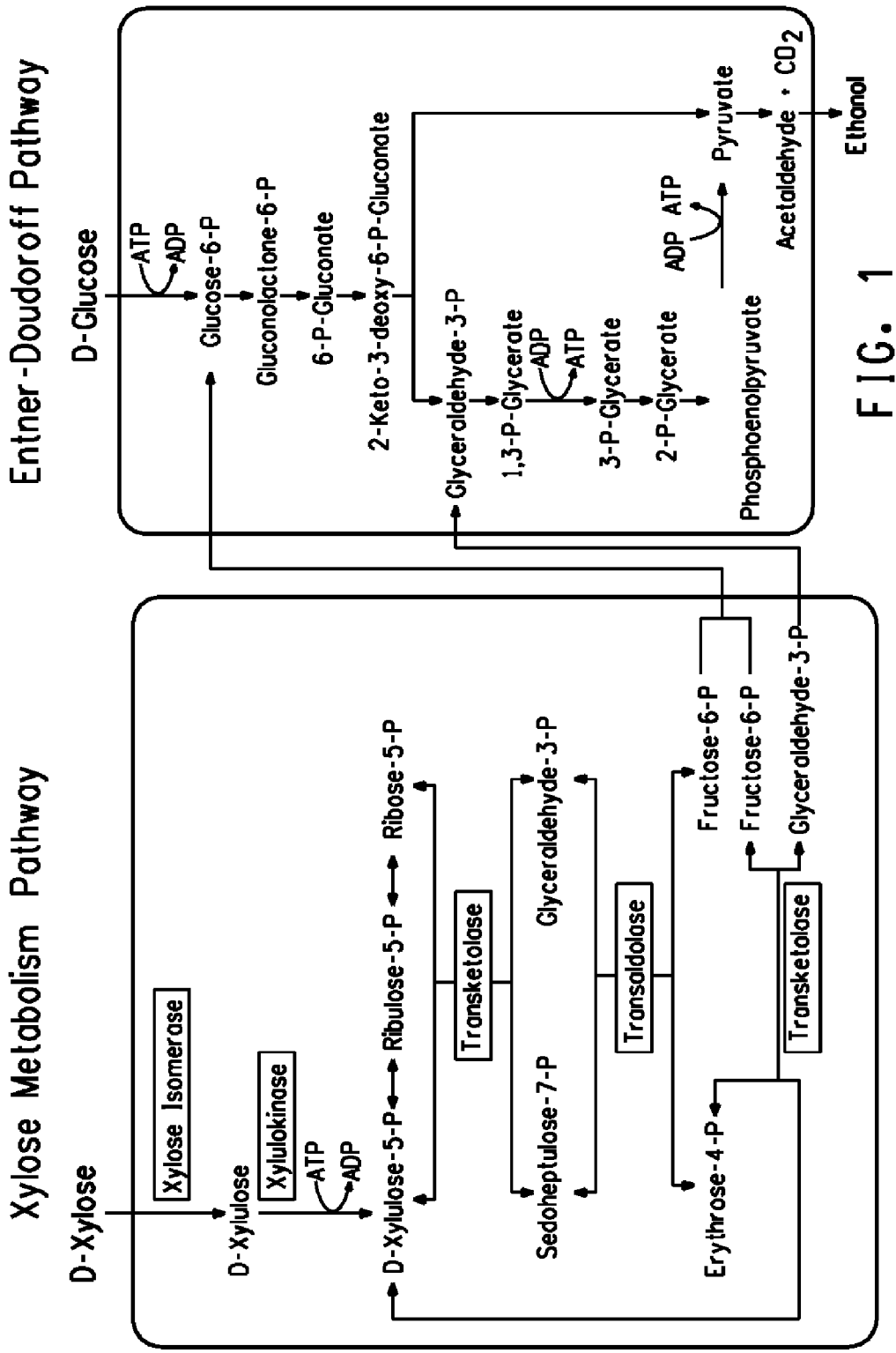
FIG. 1 shows a diagram of the ethanol fermentation pathway in *Zymomonas* engineered for xylose utilization.

The invention relates to the use of an antimicrobial agent to control contaminating bacteria in fermentations that use Zymomonas as the biocatalyst, such as for production of ethanol. The finding that virginiamycin is safe for Zymomonas cells while effectively controlling contaminating bacteria allows its use in fermentations where Zymomonas is the biocatalyst. In particular, high levels of virginiamycin, which are higher than levels typically used in fermentations for production of ethanol by yeast, are found to be required for effective control of contaminating bacteria in fermentation media containing cellulosic biomass hydrolysate. The high levels may be used in Zymomonas fermentations with no reduction in ethanol production. The efficient production of ethanol from renewable resources, such as cellulosic biomass hydrolysate, for use as a fuel additive will address shortages in fossil fuels, reduce energy costs and impact global warming.

The following definitions and abbreviations are to be use for the interpretation of the claims and the specification.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "ethanologen" refers to an organism that produces ethanol through metabolism of carbohydrate sources.

The term "fermentable sugar(s)" refers to oligosaccharides and monosaccharides that can be used as a carbon source by a microorganism in a fermentation process.

The term "simultaneous saccharification and fermentation (SSF)" refers to a process wherein biomass is saccharified and the fermentable sugars produced from saccharification are used by a biocatalyst to produce a product all at the same time, typically in the same reaction vessel.

The term "cellulosic" refers to a composition comprising cellulose and additional components that may include hemicellulose and lignin.

The term "lignocellulosic" refers to a composition comprising both lignin and cellulose. Lignocellulosic material may also comprise hemicellulose.

The term "saccharification" refers to the production of fermentable sugars from polysaccharides.

The term "biomaterial" refers to any biologically derived material that is a source of carbohydrates that may be used in fermentation by a biocatalyst. Biomaterial includes cellulosic biomass as well as other plant materials and plant-derived materials used as carbohydrate sources such as grains, mash, molasses, and raw juice (such as from sugar beets and sugar cane).

The term "pretreated biomass" means biomass that has been subjected to pretreatment prior to saccharification.

The term "cellulosic biomass" refers to any cellulosic or lignocellulosic material and includes materials comprising cellulose, and optionally further comprising hemicellulose, lignin, starch, oligosaccharides and/or monosaccharides. Cellulosic biomass may also comprise additional components, such as protein and/or lipid. Cellulosic biomass may be derived from a single source, or can comprise a mixture derived from more than one source; for example, cellulosic biomass could comprise a mixture of corn cobs and corn stover, or a mixture of grass and leaves. Cellulosic biomass includes, but is not limited to, bioenergy crops, agricultural residues, municipal solid waste, industrial solid waste, sludge from paper manufacture, yard waste, wood and forestry waste. Examples of cellulosic biomass include, but are not limited to, corn cobs, crop residues such as corn husks, corn stover, grasses, wheat, wheat straw, barley straw, hay, rice straw, switchgrass, palm frond, empty palm fruit bunches, waste paper, sugar cane bagasse, sorghum or soy cellulosic plant material, cellulosic components obtained from milling of grains, trees, branches, roots, leaves, wood chips, sawdust, shrubs and bushes, vegetables, fruits, flowers and animal manure.

The term "cellulosic biomass hydrolysate" refers to the product resulting from saccharification of cellulosic or lignocellulosic biomass. The biomass may also be pretreated prior to saccharification. Cellulosic biomass hydrolysate is a product containing biomass solids.

The term "clarified cellulosic biomass hydrolysate" or "clear cellulosic biomass hydrolysate" refers to a cellulosic biomass hydrolysate which has been processed to remove solids and is not considered to be a cellulosic biomass hydrolysate. In addition, any preparation containing sugars derived from cellulosic biomass.

The term "saccharification enzyme" refers to an enzyme that can catalyze conversion of a component of biomass to fermentable sugars. Typically the enzyme is more effective when the biomass is pretreated.

The term "substantial contamination" refers to a level of lactic acid bacteria contamination in a fermentation broth that would produce more than about defined medium of lactic acid if the fermentation broth were incubated without an antimicrobial for about 40 hours.

The term "lactic acid bacteria" refers to bacteria that produce lactic acid as a major metabolic end-product of carbohydrate fermentation. The lactic acid bacteria (LAB) are gram positive bacteria belonging to the order Lactobacillales, and include for example the genera *Lactobacillus, Leuconostoc, Lactococcus, Pediococcus, Streptococcus*, and *Enterococcus*.

The term "fermentation medium" refers to a composition comprising components, such as nutrients, that support the growth of a microorganism used as a biocatalyst. Fermentation medium may be used in any size including small scale cultures and large scale production fermentations.

The term "fermentation broth" refers to a composition comprising fermentation medium and biocatalyst cells in which fermentation is occurring or has occurred. Depending on how long the biocatalyst has been grown in the fermentation broth, this broth may also include the product produced by the biocatalyst, such as ethanol.

The term "seed culture" is a culture of biocatalyst cells that is used to inoculate a larger volume of fermentation medium producing a fermentation broth. Typically a seed culture inoculum is about 0.01% to 20% v/v of the final volume of the fermentation broth.

The term "contamination" refers to the presence of microorganisms that are not intentionally introduced. Typically a desired biocatalyst is introduced into a growth medium producing a fermentation broth. Microorganisms present in the fermentation broth other than the introduced biocatalyst are considered to be contamination.

The present method provides for control of undesired bacteria in cultures where a *Zymomonas* bacterium is the biocatalyst, such as in fermentation for ethanol production. Undesired, contaminating bacteria are typically present in large scale processes, particularly when media contain processed biomaterial. Processed biomaterial used in media may include carbohydrate sources such as corn or wheat mash, sugar beet or sugar cane molasses, and cellulosic or lignocellulosic biomass hydrolysate. Contaminating bacteria may be introduced in a fermentation process from biomaterial, process equipment, inoculation cultures, process water, air, or other sources. Controlling contamination in a production fermentation typically allows the biocatalyst to grow and produce product to a higher level than that achieved in the presence of contaminating bacteria, providing a more efficient and economical fermentation process.

Antimicrobial Agent for *Zymomonas* Fermentations

Since *Zymomonas* itself is a bacterium, for an antimicrobial agent to be used in *Zymomonas* fermentations it must selectively target the contaminating bacteria while not affecting the *Zymomonas* bacteria. The predominant contaminating bacteria in large-scale fermentations using biomaterial-derived carbohydrate sources are lactic acid bacteria (LAB), such as strains of *Lactobacillus*. LAB are gram positive while *Zymomonas* is gram negative. The challenge was thus to identify an antimicrobial agent that controls LAB in fermentation media, without negative impact on growth and ethanol production of *Zymomonas* cells. Other contaminating bacteria in addition to LAB may be controlled by this type of antimicrobial agent.

The present method uses virginiamycin as a selective antimicrobial agent in *Zymomonas* fermentations. It is found herein that virginiamycin is safe for use to control contamination in *Zymomonas* cultures. Virginiamycin is produced by *Streptomyces virginiae* and is commercially available in different preparations such as Lactrol® (Phibro; Ridgefield Park, N.J.) and Lactoside V™ (Lallemand Ethanol Technology; Milwaukee, Wis.). Lactrol® is recommended for use in ethanol fermentations where yeast is the biocatalyst at 0.25 parts per million (ppm) to 2.0 ppm, with 0.5 ppm being most commonly used. Manufacturer instructions indicate that dosage should not exceed 6.0 ppm during fermentation. The Lactrol® specifications indicate that the preparation is 100% activity, indicating that 2 ppm of Lactrol® is equivalent to 2 ppm of virginiamycin. Lactoside V™ is recommended for use in ethanol fermentations where yeast is the biocatalyst at 0.1 ppm to 3.0 ppm. In addition, Lactoside 247™ (Lallemand Ethanol Technology; Milwaukee, Wis.) contains virginiamycin that is combined with penicillin G. Manufacturer instructions recommend use in ethanol fermentations where yeast is the biocatalyst at 1 to 2 ppm, with higher rates potentially required for severe infections.

In one aspect, in the present methods virginiamycin and an inoculum of *Zymomonas* cells are added to a fermentation medium producing a fermentation broth, which is maintained under conditions suitable for growth of the *Zymomonas* cells. The virginiamycin and inoculum may be added to the medium in either order, or concurrently. The present fermentation broth compositions comprise fermentation medium, virginiamycin, and a growing population of *Zymomonas* cells as described below. Once the fermentation medium is inoculated with *Zymomonas* cells such as cells from a freezer stock, cells revived from a freezer stock, or cells in a seed culture, the *Zymomonas* cells grow forming a growing population of *Zymomonas* cells.

The fermentation medium may be of any type that supports growth and production by *Zymomonas* cells. One skilled in the art will know how to prepare any of the described types of media in view of the information below. In one embodiment the fermentation medium is a defined medium. This medium contains typical purchased components including a carbohydrate source such as glucose, a source of amino acids and other nutrients such as yeast extract, and other components that may include trace elements, nitrogen, and phosphorus such as $KH_2PO_4$ and $MgSO_4$. Defined medium is often used for growing laboratory scale cultures as well as seed cultures that are used as inoculum for large scale fermentations.

In another embodiment the fermentation medium contains sugars obtained from non-cellulosic materials such as mash, raw juice, or molasses. These sugars are prepared from biomaterials such as cereal grains (such as corn, wheat, barley, and rye), and sugar crops such as sugar beets and sugar cane. Hydrolyzed mash used for fermentation is made from cereal grains typically by heating to a temperature above the gelatinization temperature, treating with alpha amylase to liquefy, and saccharifying using enzymes such as glucoamylase. Molasses or raw juice from sugar beets and sugar cane may be used as the sugar source in fermentation medium. This type of sugar source is a non-cellulosic biomaterial sugar source (cellulosic includes lignocellulosic), since the sugar source is primarily starch or sugar juice. This type of sugar source is typically used in seed cultures and in the production of ethanol using yeast as a biocatalyst, and in other non-cellulosic large scale fermentations.

Defined media and media having sugar from a non-cellulosic source lack cellulosic (including lignocellulosic) biomass hydrolysate. Additionally, media containing a sugar source that is obtained from cellulosic biomass, and is highly purified to remove other cellulosic components such as solids, is considered to be medium lacking cellulosic biomass hydrolysate. This type of medium contains a clarified cellulosic biomass hydrolysate.

In yet another embodiment the fermentation medium contains cellulosic biomass hydrolysate prepared from cellulosic (including lignocellulosic) biomaterials. Cellulosic biomass hydrolysate contains biomass solids. Cellulosic biomass hydrolysate is produced by saccharification of cellulosic (including lignocellulosic) biomass. Typically the biomass is pretreated prior to saccharification. Biomass may be treated by any method known by one skilled in the art to produce fermentable sugars in a hydrolysate. Typically the biomass is pretreated using physical and/or chemical treatments, and saccharified enzymatically. Physical and chemical treatments may include grinding, milling, cutting, base treatment such as with ammonia or NaOH, and/or acid treatment. Particularly useful is a low ammonia pretreatment where biomass is contacted with an aqueous solution comprising ammonia to form a biomass-aqueous ammonia mixture where the ammonia concentration is sufficient to maintain an alkaline pH of the biomass-aqueous ammonia mixture but is less than about 12 wt. % relative to dry weight of biomass, and where dry weight of biomass is at least about 15 wt % solids relative to the weight of the biomass-aqueous ammonia mixture, as disclosed in commonly owned U.S. Pat. No. 7,932,063, which is herein incorporated by reference.

Enzymatic saccharification typically makes use of an enzyme composition or blend to break down cellulose and/or hemicellulose and to produce a hydrolysate containing sugars such as, for example, glucose, xylose, and arabinose. Saccharification enzymes are reviewed in Lynd, L. R., et al. (Microbiol. Mol. Biol. Rev., 66:506-577, 2002). At least one enzyme is used, and typically a saccharification enzyme blend is used that includes one or more glycosidases. Glycosidases hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223:1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650 1999, respectively]) of the general group "hydrolases" (EC 3.). Glycosidases useful in the present method can be categorized by the biomass components they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabino-xylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), or feruloyl esterases (EC 3.1.1.73) to promote the release of polysaccharides from other components of the biomass. It is known in the art that microorganisms that produce polysaccharide-hydrolyzing enzymes often exhibit an activity, such as a capacity to degrade cellulose, which is catalyzed by several enzymes or a group of enzymes having different substrate specificities. Thus, a "cellulase" from a microorganism may comprise a group of enzymes, one or more or all of which may contribute to the cellulose-degrading activity. Commercial or non-commercial enzyme preparations, such as cellulase, may comprise numerous enzymes depending on the purification scheme utilized to obtain the enzyme. Many glycosyl hydrolase enzymes and compositions thereof that are useful for saccharification are disclosed in WO 2011/038019.

Saccharification enzymes may be obtained commercially. Such enzymes include, for example, Spezyme® CP cellulase, Multifect® xylanase, Accelerase® 1500, and Accellerase® DUET (Danisco U.S. Inc., Genencor International, Rochester, N.Y.), and Novozyme-188 (Novozymes, 2880 Bagsvaerd, Denmark). In addition, saccharification enzymes may be unpurified and provided as a cell extract or a whole cell preparation. The enzymes may be produced using recombinant microorganisms that have been engineered to express one or more saccharifying enzymes. For example, the H3A protein preparation used herein for saccharification of pretreated cellulosic biomass is an unpurified preparation of enzymes produced by a genetically engineered strain of *Trichoderma reesei*, which includes a combination of cellulases and hemicellulases and is described in WO 2011/038019, which is incorporated herein by reference.

Additional enzymes for saccharification include, for example, glycosyl hydrolases such as members of families GH3, GH39, GH43, GH55, GH10, and GH11. GHs are a group of enzymes that hydrolyze the glycosidic bond between two or more carbohydrates, or between a carbohydrate and a noncarbohydrate moiety. Families of GHs have been classified based on sequence similarity and the classification is available in the Carbohydrate-Active enzyme (CAZy) database (Cantarel et al. (2009) Nucleic Acids Res. 37 (Database issue):D233-238). Certain of these enzymes are able to act on various substrates and have demonstrated effecacy as saccharification enzymes. Glycoside hydrolase family 3 ("GH3") enzymes have a number of known activities, including, for example, 3-glucosidase (EC:3.2.1.21); β-xylosidase (EC:3.2.1.37); N-acetyl β-glucosaminidase (EC: 3.2.1.52); glucan β-1,3-glucosidase (EC:3.2.1.58); cellodextrinase (EC:3.2.1.74); exo-1,3-1,4-glucanase (EC:3.2.1); and/or β-galactosidase (EC 3.2.1.23) activities. Glycoside hydrolase family 39 ("GH39") enzymes also have a number of known activities, including, for example, α-L-iduronidase (EC:3.2.1.76) and/or β-xylosidase (EC:3.2.1.37) activities. Glycoside hydrolase family 43 ("GH43") enzymes have a number of known activities including, for example, L-α- arabinofuranosidase (EC 3.2.1.55); β-xylosidase (EC 3.2.1.37); endoarabinanase (EC 3.2.1.99); and/or galactan 1,3-β-galactosidase (EC 3.2.1.145) activities. Glycoside hydrolase family 51 ("GH51") enzymes are known to have, for example, L-α-arabinofuranosidase (EC 3.2.1.55) and/or endoglucanase (EC 3.2.1.4) activities. Glycoside hydrolase family 10 ("GH10") have been described in detail in Schmidt et al., 1999, Biochemistry 38:2403-2412 and Lo Leggio et al., 2001, FEBS Lett 509: 303-308) and the Glycoside hydrolase family 11 ("GH11") have been described in Hakouvainen et al., 1996, Biochemistry 35:9617-24.

Fermentation media containing biomass hydrolysate may contain a percent of hydrolysate with one or more additional sugars and/or other added components, or the media may contain 90% or more hydrolysate with minor additions such as sorbitol, as described below. In various embodiments cellulosic biomass hydrolysate is at least about 50%, 60%, 79%, 80%, 90% or 95% of the final volume of fermentation broth. Typically about 10% of the final volume of fermentation broth is seed inoculum.

The solids content of biomass hydrolysate is typically between about 10% and 40%, depending on the pretreatment and saccharification methods employed. More typically the solids content is about 25%, with a medium containing 90% cellulosic biomass hydrolysate having about 23% solids.

Virginiamycin Concentrations Used in Fermentation Broths

The concentration of virginiamycin that is needed to control contamination in a *Zymomonas* fermentation broth was found herein to vary, depending on whether the fermentation medium contains cellulosic biomass hydrolysate. It is found herein that in fermentation broth containing media lacking cellulosic biomass hydrolysate (described above), a concentration of about 2 ppm of virginiamycin controls contaminating bacteria without affecting the glucose utilization and ethanol production of *Zymomonas* cells. The concentration of virginiamycin in the present fermentation broth lacking cellulosic biomass hydrolysate may be at least about 0.25 ppm, 0.5 ppm, 0.75 ppm, 1 ppm, 2 ppm, 3 ppm, 4 ppm, 5 ppm, 10 ppm, or 20 ppm, including any integer or fraction therebetween. Typical embodiments use virginiamycin at concentrations that are between about 0.25 ppm and 20 ppm. More typical embodiments use virginiamycin at concentrations that are between about 1.0 ppm and 10 ppm. The amount of virginiamycin needed to control contamination depends on factors such as the amount of contamination, type of medium, concentration of *Zymomonas* cells following inoculation, and the fermentation conditions, and can be determined by one skilled in the art for a specific situation.

Control of contaminating bacteria may be assessed by determining the level of lactic acid in the fermentation broth, where the presence of less than about 5 g/L of lactic acid after about 40 hours of fermentation indicates that contamination is controlled. Contamination may be controlled at less than about 5 g/L of lactic acid in the fermentation broth, or less than 4 g/L or 3 g/L or 2 g/L or 1 g/L of lactic acid. The amount of lactic acid in fermentation broth is typically assayed by HPLC, as is known by one skilled in the art.

In media lacking cellulosic biomass hydrolysate and containing 2.5 ppm or 5 ppm of virginiamycin, growth of *Zymomonas* cells was found herein to be better than growth of the cells in the absence of virginiamycin as measured by $OD_{600}$. In one embodiment growth of *Zymomonas* cells is improved by growing the cells in medium comprising virginiamycin. Improved growth may contribute to reducing contamination level through competition, and/or to increasing ethanol production. The concentration of virginiamycin used to improve growth depends on factors such as the type of medium used, the concentration of *Zymomonas* cells following inoculation, and the fermentation conditions. One of skill in the art can readily assess the concentration of virginiamycin that stimulates *Zymomonas* cell growth when using a specific medium and set of conditions for fermentation. For example, in clarified cellulosic biomass hydrolysate medium under conditions described in Example 1 herein, virginiamycin concentrations of 2.5 ppm and 5 ppm improved growth of *Zymomonas* cells. In other fermentations *Zymomonas* cell growth may be improved by the presence of virginiamycin in concentration in the range of about 1 ppm to about 50 ppm, or more.

It is found herein that when contamination present in a seed culture is controlled by using virginiamycin (as described above), and the seed culture is used to inoculate a larger scale fermentation, contamination remains controlled in the large scale fermentation without adding virginiamycin or other anti-microbial agent to the fermentation medium separately from the inoculum. Thus in one embodiment, contamination is controlled in a fermentation by the inclusion of virginiamycin in a seed culture that is used to inoculate the fermentation medium. The fermentation medium may contain cellulosic biomass hydrolysate, or lack cellulosic biomass hydrolysate. In a seed culture grown in medium lacking cellulosic biomass hydrolysate, the concentration of virginiamycin may be as descried above: at least about 0.25 ppm, 0.5 ppm, 0.75 ppm, 1 ppm, 2 ppm, 3 ppm, 4 ppm, 5 ppm, 10 ppm, or 20 ppm, including any integer or fraction therebetween. Typical embodiments use virginiamycin at concentrations that are between about 0.25 ppm and 20 ppm. More typical embodiments use virginiamycin at concentrations that are between about 1 ppm and about 5 ppm.

However when contamination is not controlled in a seed culture, contamination is a factor in a large scale fermentation that is inoculated with the contaminated seed culture. In one embodiment contamination in the contaminated seed-inoculated fermentation is controlled as described above when using medium lacking cellulosic biomass hydrolysate.

It is found herein that in fermentation broth containing media containing cellulosic biomass hydrolysate, a concentration of virginiamycin that is at least about 10 ppm can be used to control contaminating bacteria while maintaining typical ethanol production by the *Zymomonas* cells (about 70 to 80 g/L for the *Zymomonas* strain used herein). In various embodiments of the present fermentation broth containing cellulosic biomass hydrolysate, the virginiamycin concentration in the fermentation broth is at least about 10 ppm, 20 ppm, 30 pm, 40 ppm, 50 ppm, 100 ppm, 150 ppm, 200 ppm, or 250 ppm, including any integer or fraction therebetween. It is found herein that good ethanol production is achieved by *Zymomonas* cells in contaminated-seed-inoculated fermentation broth comprising medium containing cellulosic biomass hydrolysate and virginiamycin concentrations from 10 ppm through 250 ppm. The presence of relatively high solids in cellulosic biomass hydrolysate containing medium may contribute to the requirement for the higher levels of virginiamycin needed to control contamination as compared to levels that are effective in medium lacking cellulosic biomass hydrolysate. The presence of various biomass degradation products in hydrolysate may also contribute. The high levels of virginiamycin are greater than those recommended for use in yeast ethanol production by the manufacturers of virginiamycin products.

In any type of medium used for fermentation, specific contamination control results will depend on factors including growth and production characteristics of the *Zymomonas* strain used, the contaminating microorganisms present, the initial contamination level, the type and amount of cellulosic biomass hydrolysate in the medium (includes percent solids and toxicity of hydrolysate by-products to contaminating and *Zymomonas* cells) if present, and culture conditions including mixing. One of skill in the art can readily determine the concentration of virginiamycin relative to the amounts disclosed herein that is effective in controlling contamination in a specific *Zymomonas* fermentation broth using specific fermentation conditions, while maintaining *Zymomonas* cell productivity.

Inoculum of *Zymomonas* Cells

In the present method the inoculum of *Zymomonas* cells may be any source of *Zymomonas* cells that is effective in starting a growing culture. Typically, *Zymomonas* cells are stored as frozen stocks, and cells are revived by growing in a small culture in defined medium. The small culture is used as an inoculum that is added to fermentation medium to produce a fermentation broth, or culture. A small culture may also be used to inoculate a seed culture. The *Zymomonas* cells are grown in the seed culture, which is then added as an inoculum to a larger scale fermentation. A seed culture used as an inoculum may contain sterile defined medium with no virginiamycin needed to control contamination. Alternatively, a seed culture used as an inoculum may contain defined medium or other medium lacking cellulosic biomass hydrolysate, such as medium prepared from mash or molasses, that may be contaminated such as by process equipment, where virginiamycin is added to control contamination as described above. In addition, a seed culture used as an inoculum may contain cellulosic biomass hydrolysate and virginiamycin to control contamination as described above.

*Zymomonas* Cells

Any strain of *Zymomonas* cells may be used in the present compositions and methods, and is selected based on factors including the type of medium to be used and the desired output of the fermentation process. Any strain of *Zymomonas* that is an effective biocatalyst for the desired production process may be used. For example, *Zymomonas* cells naturally produce ethanol using glucose, fructose and/or sucrose as fermentation substrates, but xylose is not metabolized. In one embodiment the *Zymomonas* cells used in the present methods and compositions have been engineered for xylose utilization, which is particularly desired when using cellulosic biomass hydrolysate, which contains xylose.

Strains of ethanol-producing *Zymomonas*, such as *Z. mobilis* have been engineered for xylose fermentation to ethanol. Typically four genes have been introduced into *Z. mobilis* for expression of four enzymes involved in xylose metabolism to create a xylose utilization metabolic pathway (FIG. 1) as described in U.S. Pat. No. 5,514,583, U.S. Pat. No. 5,712,133, U.S. Pat. No. 6,566,107, WO 95/28476, Feldmann et al. ((1992) Appl Microbiol Biotechnol 38: 354-361), and Zhang et al. ((1995) Science 267:240-243). These include genes encoding xylose isomerase which catalyzes the conversion of xylose to xylulose, and xylulokinase which phosphorylates xylulose to form xylulose 5-phosphate. Additionally expressed are transketolase and transaldolase, two enzymes of the pentose phosphate pathway that convert xylulose 5-phosphate to intermediates that couple pentose metabolism to the glycolytic Entner-Douderoff pathway permitting the metabolism of xylose to ethanol (see FIG. 1). DNA sequences encoding these enzymes may be obtained from any of numerous microorganisms that are able to metabolize xylose, such as enteric bacteria, and some yeasts and fungi. Sources for the coding regions may include *Xanthomonas*, *Klebsiella*, *Escherichia*, *Rhodobacter*, *Flavobacterium*, *Acetobacter*, *Gluconobacter*, *Rhizobium*, *Agrobacterium*, *Salmonella*, *Pseudomonads*, and *Zymomonas*. The coding regions of *E. coli* are typically used.

The encoding DNA sequences are operably linked to promoters that are expressed in *Zymomonas* cells such as the promoter of *Z. mobilis* glyceraldehyde-3-phosphate dehydrogenase (GAP promoter), and *Z. mobilis* enolase (ENO promoter). A mutant GAP promoter with increased expression as disclosed in U.S. Pat. No. 7,989,206, which is incorporated herein by reference, is also useful for expression in *Zymomonas*. The coding regions may individually be expressed from promoters, or two or more coding regions may be joined in an operon with expression from the same promoter. The resulting chimeric genes may be introduced into *Zymomonas* cells and maintained on a plasmid, or integrated into the genome using, for example, homologous recombination, site-directed integration, or random integration. Examples of strains engineered to express a xylose utilization metabolic pathway include CP4(pZB5) (U.S. Pat. No. 5,514,583), ATCC31821/pZB5 (U.S. Pat. No. 6,566,107), 8b (US 20030162271; Mohagheghi et al., (2004) Biotechnol. Lett. 25; 321-325), and ZW658 (ATTCC # PTA-7858). Cells of *Zymomonas* that are engineered for expression of the xylose utilization metabolic pathway generally require a period of adaptation in xylose-containing medium prior to being able to grow in medium that contains xylose as the only sugar.

In additional embodiments the *Zymomonas* cells have one or more additional genetic modification that improves the strain such as one that increases growth rate and/or cell mass, increases utilization of xylose and/or allows use of other sugars such as arabinose, increases tolerance to inhibitory compounds such as acetate, or increases production of ethanol.

In one embodiment *Zymomonas* cells may be additionally engineered for arabinose utilization which is described in U.S. Pat. No. 5,843,760, which is incorporated herein by reference. To allow arabinose utilization, genes expressed in addition to genes of the xylose utilization pathway include:1) L-arabinose isomerase to convert L-arabinose to L-ribulose, 2) L-ribulokinase to convert L-ribulose to L-ribulose-5-phosphate, and 3) L-ribulose-5-phosphate-4-epimerase to convert L-ribulose-5-phosphate to D-xylulose (U.S. Pat. No. 5,843,760). As disclosed in US 2011/0143408, which is incorporated herein by reference, improved arabinose utilization may be achieved by additionally expressing an arabinose-proton symporter, such as by expressing a coding region from an araE gene.

In another embodiment the endogenous himA gene, which encodes the alpha subunit of the integration host factor, is genetically modified to reduce its expression which improves growth in medium containing acetate as described in U.S. Pat. No. 7,897,396, which is incorporated herein by reference. Acetate is present in biomass hydrolysate, thus when using medium containing biomass hydrolysate, increased tolerance to this component is desired.

In another embodiment a genetic modification is made that reduces glucose-fructose oxidoreductase (GFOR) activity as described in U.S. Pat. No. 7,741,119, which is incorporated herein by reference. Reduced expression of GFOR, as well as of the himA gene, may be by any method such as those described above for reducing aldose reductase activity.

In another embodiment a genetic modification is made which increases ribose-5-phosphate isomerase (RPI) activity, as disclosed in commonly owned and co-pending U.S. patent application Ser. No. 13/161,734, which is incorporated herein by reference. Increased RPI expression may be accomplished by increasing expression of the endogenous RPI encoding gene, such as with a promoter that is more highly active than the native promoter, or by expressing a heterologous gene encoding any protein or polypeptide with ribose-5-phosphate isomerase activity in *Zymomonas*. There are two groups of ribose-5-phosphate isomerase enzymes that are called RPI-A and RPI-B, as described in U.S. application Ser. No. 13/161,734, either of which may be expressed.

In another embodiment, the xylose isomerase that is expressed as part of the xylose utilization metabolic pathway is expressed using a mutant, highly active promoter that is disclosed in U.S. Pat. No. 7,989,206 and U.S. Pat. No. 7,998,722, which are incorporated herein by reference. The mutant promoters disclosed therein are promoters of the *Zymomonas mobilis* glyceraldehyde-3-phosphate dehydrogenase gene.

In another embodiment a xylose isomerase that is expressed as part of the xylose utilization metabolic pathway is a Group I xylose isomerase included in the class of enzymes identified by EC 5.3.1.5 as disclosed in commonly owned and co-pending US Patent Publication US 2011-0318801. It is disclosed therein that Group I xylose isomerases, such as one expressed from a coding region isolated from *Actinoplanes missouriensis* have higher activity in *Zymomonas* than Group 2 xylose isomerase. Group I xylose isomerases. are defined therein by molecular phylogenetic bioinformatics analysis (using PHYLIP neighbor joining algorithm as implemented in PHYLIP (Phylogeny Inference Package version 3.5c; Felsenstein (1989) Cladistics 5:164-166), GroupSim analysis (Capra and Singh (2008) Bioinformatics 24: 1473-1480), and a Profile Hidden Markov Model (using the hmmsearch algorithm of the HMMER software package; Janelia Farm Research Campus, Ashburn, Va.).

In another embodiment the *Zymomonas* cells have been adapted for growth in a stress culture containing ethanol and ammonium acetate as disclosed in US Patent Application Publication 2011-0014670-A1, which is incorporated herein by reference. These *Zymomonas* strains with improved acetate tolerance are particularly useful when using cellulosic biomass hydrolysate containing fermentation medium, which contains acetate.

Strains disclosed in the above references provide examples of strains that may be used in the present methods and include ATCC31821/pZB5, ZW658 (ATCC #PTA-7858), ZW800, ZW801-4, ZW801-4:: ΔhimA, AcR#3, and ZW705.

*Zymomonas* Fermentation

In the present method the inoculated culture medium, or fermentation broth, is incubated under conditions suitable for growth of *Zymomonas* cells. In one embodiment the *Zymomonas* cells are of a strain of *Zymomonas* that is an effective biocatalyst for the production of ethanol under conditions used in fermentation, and ethanol is produced in the fermentation broth. When the sugars concentration in the fermentation medium is high such that growth is inhibited, the medium includes sorbitol, mannitol, or a mixture thereof as disclosed in commonly owned U.S. Pat. No. 7,629,156, which is incorporated herein by reference. Typically a final concentration of about 5 mM sorbitol or mannitol is present in the medium.

Typically conditions are used with temperature that is between about 30° C. and about 37° C., and with pH of about 4.5 to about 7.5. Typically cultures are incubated without supplemented air, oxygen, or other gases (which may include conditions such as anaerobic, microaerobic, or microaerophilic fermentation), for at least about 20 hours, and may be run for about 25, 30, 35, 40, 45, 50, 55, 60, 65, 70 hours or longer. Typically seed cultures are incubated for about 20 hours, while fermentation production cultures are incubated for about 40 hours or more. In order to minimize foaming, antifoam agents (any class-silicone based, organic based etc) may be added to the medium as needed.

For commercial production fermentation cultures, a variety of culture methodologies may be applied. For example, large-scale production may use both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of ethanol.

A variation on the standard batch system is the Fed-Batch system. Fed-Batch culture processes are also suitable for the present methods and compositions, and comprise a typical batch system with the exception that the substrate is added in increments as the culture progresses. Measurement of the actual substrate concentration in Fed-Batch systems is difficult and is therefore estimated on the basis of the changes of measurable factors such as pH and the partial pressure of waste gases such as $CO_2$. Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., *Appl. Biochem. Biotechnol.*, 36, 227, (1992).

The present methods and compositions may also be used in a continuous culture process. Continuous cultures are open systems where culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials as is known to one skilled in the art.

In a production process, production fermentation cultures are typically run one after the other until a clean-out of the system is necessary.

The present methods and compositions may also be used in a simultaneous saccharification and fermentation (SSF) process. For example, the process disclosed in US Patent Application Publication 2011-0318803, which is incorporated herein by reference, may be used. In this SSF process *Zymomonas* cells are grown under conditions of low impeller agitation with high concentration of insoluble solids in a saccharification-fermentation mixture during a simultaneous saccharification and fermentation reaction for the production of high concentrations of ethanol. In addition, a hybrid saccharification and fermentation (HSF) process may be used in which partial saccharification is carried out prior to addition of *Zymomonas* cells, then further saccharification and fermentation occur simultaneously.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "hr" means hour(s), "min" means minute(s), "sec" means second(s), "d" means day(s), "L" means liter(s), "mL" means milliliter(s), "µL" means microliter(s), "g" means grams, "µg" means microgram(s), "ng" means nanogram(s), "g/L" means grams per liter, "mM" means millimolar, "µM" means micromolar, "nm" means nanometer(s), "µmol" means micromole(s), "pmol" means picomole(s), "OD600" means optical density measured at 600 nm, "EFT" means elapsed fermentation time, "ppm" means parts per million.

General Methods
Strain ZW705 Description

*Zymomonas mobilis* strain ZW705 was produced from strain ZW804-1. ZW801-4 is a recombinant xylose-utilizing strain of *Z. mobilis* that was described in commonly owned U.S. Pat. No. 7,741,119, which is incorporated herein by reference. Strain ZW801-4 was derived from strain ZW800, which was derived from strain ZW658, all as described in U.S. Pat. No. 7,741,119. ZW658 was constructed by integrating two operons, $P_{gap}$xylAB and $P_{gap}$talkt, containing four xylose-utilizing genes encoding xylose isomerase, xylulokinase, transaldolase and transketolase, into the genome of ZW1 (ATCC 31821) via sequential transposition events, and followed by adaptation on selective media containing xylose (U.S. Pat. No. 7,629,156). ZW658 was deposited as ATCC PTA-7858. In ZW658, the gene encoding glucose-fructose oxidoreductase was insertionally-inactivated using host-mediated, double-crossover, homologous recombination and spectinomycin resistance as a selectable marker to create ZW800 (U.S. Pat. No. 7,741,119). The spectinomycin resistance marker, which was bounded by loxP sites, was removed by site specific recombination using Cre recombinase to create ZW801-4.

Cultures of *Z. mobilis* strain ZW801-4 were adapted for growth under stress conditions of medium containing ammonium acetate to produce ZW705 as described in US Patent Application Publication 2011-0014670, which is incorporated herein by reference. A continuous culture of ZW801-4 was run in 250 ml stirred, pH and temperature controlled fermentors (Sixfors; Bottmingen, Switzerland). The basal medium for fermentation was 5 g/L yeast extract, 15 mM ammonium phosphate, 1 g/L magnesium sulfate, 10 mM sorbitol, 50 g/L xylose and 50 g/L glucose. Adaptation to growth in the presence of high concentrations of acetate and ammonia was effected by gradually increasing the concentration of ammonium acetate added to the above continuous culture media while maintaining an established growth rate as measured by the specific dilution rate over a period of 97 days. Ammonium acetate was increased to a concentration of 160 mM. Further increases in ammonium ion concentration were achieved by addition of ammonium phosphate to a final total ammonium ion concentration of 210 mM by the end of 139 days of continuous culture. Strain ZW705 was isolated from the adapted population by plating to single colonies and amplification of one chosen colony.

Cob Composition

The amount of cellulose and xylan in starting corn cob was determined using the method ASTM E1758-01 "Standard method for the determination of carbohydrates by HPLC" as further detailed n National Renewable Energy Lagoratory (Golden, Colo.) Technical Report NREL/TP-510-42618 (revised April 2008). The composition was determined to be 34.8% cellulose, 29.2% xylan, 12.8% lignin based on dry weight.

Saccharification Enzymes

Spezyme® CP cellulase and Multifect®-CX12L was from Danisco U.S. Inc., Genencor International, Rochester, N.Y. Novozyme-188 was from Novozymes (2880 Bagsvaerd, Denmark).

H3A Protein

H3A protein was prepared from the genetically engineered H3A strain of *Trichoderma reesei*. Strain H3A was prepared as described in U.S. Pat. No. 7,666,648. Briefly, a *Trichoderma reesei* mutant strain, derived from RL-P37 (Sheir-Neiss, G et al. Appl. Microbiol. Biotechnol. 1984, 20:46-53) and selected for high cellulase production was co-transformed with a β-glucosidase expression cassette and an endoxylanase expression cassette using electroporation. One transformant was called strain #229. Strain #229 was co-transformed with a β-xylosidase Fv3A expression cassette, a β-xylosidase Fv43D expression cassette, and a Fv51A α-arabinofuranosidase expression cassette using electroporation. Strain H3A was isolated from this transformation step.

Extracellular proteins produced during fermentation of strain H3A were separated from the cell mass by centrifugation, concentrated by membrane-ultrafiltration through a Millipore 10 kD molecular cut off weight membrane, and pH adjusted to 4.8. Total protein was determined using a modified Biuret method as modified by Weichselbaum and Gornall using Bovine Serum Albumin as a calibrator (Weichselbaum, 1960, Amer. J. Clin. Path. 16:40; Gornall et al., 1949 J. Biol. Chem. 177:752). This H3A extracellular protein preparation, also termed herein as H3A protein, was used as a combination cellulase and hemicellulase preparation effecting complex carbohydrate hydrolysis during SSF.

Cob Hydrolysate FRF13
Pretreatment

Corn cob hydrolysate was prepared first by dilute ammonia pretreatment of ground corn cob using low ammonia methods described in U.S. Pat. No. 7,932,063. A horizontal Littleford Day 130 L reactor vessel containing a jacket for passing steam around the body of the vessel (Littleford Day, Inc., Florence, Ky.) was used for pretreatment to generate pretreated cob named SSL34. The vessel was loaded with cob from seed corn processing to reach 46 v % reactor fill on a wet cob basis (51 lbs). The cob had been reduced to less than 1 mm in size using a large micropulverizer (Model #1SH, Serial #10019; Pulverizing Machinery Co., Summit, N.J.) with a 1.0 mm screen. A scoop of dry ice was added as needed to the cob before grinding to prevent the equipment from heating up. The main drive of the micropulverizer is a 5 h.p. motor, with a maximum rotor speed of 9,600 RPM. It has six rotating hammers, a shell, and is lined with opposing impact edges.

The cob had a wet loose bulk density of 0.385 g/cm³ and 7.4 wt % moisture. Vacuum was applied to the vessel to reach 0.1 atm prior to introduction of a 28.9 wt % ammonium hydroxide solution (9.8 lbs) and water (17.9 lbs) near the top of the vessel to give 6 wt % $NH_3$ relative to dry weight biomass and 60 wt % solids inside the vessel. A second and third pretreatment batch, named SSL35 and SSL36, were performed in the same manner to generate enough material for the subsequent saccharification. In all batches, the reactor agitator was set to 70 rpm and steam was passed through the jacket of the vessel. When the vessel reached an internal temperature of 80° C. steam was introduced near the top of the vessel to raise the internal vessel temperature to 145° C. This temperature was held for 20 minutes. At 15 minutes of this hold-up time the steam flow through the jacket was stopped. At the end of pretreatment, the reactor was depressurized through a vent condenser to reach atmospheric pressure. Vacuum (approximately to less than 1 atm) was subsequently applied for 15 minutes to lower the temperature to less than 60° C. and remove additional ammonia and water from the pretreated cob prior to opening the bottom valve of the vessel and recovering the pretreated biomass. Final wt % of solids for pretreated cob batches SSL34, SSL35, and SSL36 was 67.4%, 66.2%, and 68.0%, respectively.

Saccharification

A hydrolysate (FRF13) was generated in a 200 L fermenter using a mixture of the pretreated corn cobs from SSL34, SSL 35 and SSL36 preparations by saccharifying with the H3A protein described above. A water heel (120.0 kg) was added to the fermenter and sterilized with jacket heat to 121° C., held for 20 minutes. The water was cooled to 47° C. and the pretreated cob mixture was added through a port on the top of the tank; 20.0 kg were added at this time. The pH was adjusted to 5.3 with 1N $H_2SO_4$ and the enzyme preparation was added. The enzyme dosage was 4.53 kg, which was equivalent to 14 mg of protein per g of glucan+xylan in the total cob to be added to the reactor. Over the following 12 hours, four additions of 15.0 kg cob were made to the reactor, every three hours, with the pH adjusted to 5.3 with 1N $H_2SO_4$ after each addition. The target solids loading for this run was 25 wt %. The fermenter was controlled at 47° C. and pH 5.3 for approximately 72 hours. At the end of this time period, 20 liters was drawn off for use in these experiments, and the remaining contents of the vessel were fermented. A sample of the hydrolysate was analyzed and the remainder was stored refrigerated until use. The results of the sample analysis are shown in Table 1.

TABLE 1

End of saccharification hydrolysate properties for FRF13

| | |
|---|---|
| Monomer Glucose (g/L) | 49.20 |
| Oligomer Glucose (g/L) | 20.45 |
| Monomer Xylose (g/L) | 54.97 |
| Oligomer Xylose (g/L) | 27.24 |
| Monomer Arabinose (g/L) | 5.92 |
| Oligomer Arabinose (g/L) | 4.58 |
| Solids content (wt %) | 24.1% |

Cob Hydrolysate MD07#3

Pretreatment

Batches of corn cob were processed with a hammermill (Glen Mills Inc., Clifton, N.H.), passed through a ⅜ inch (0.95 cm) or a 3/16 inch (0.48 cm) screen and treated with 6%, 8%, or 10% ammonia relative to dry weight biomass in a 170 L Jaygo reactor (Jaygo Manufacturing, Inc., Mahwah, N.J.) held at 145° C. for 20 min. Prior to injecting the aqueous ammonia the reactor was evacuated to ~0.1 bar, and after the 20 min period the reactor was flashed in 2 stages to ~0.1 bar. The final solids concentration for the pretreated cob mixture was about 60%.

Saccharification

The MD07#3 hydrolysate was generated in a 1000 L fermenter, equipped with a recirculation loop. A water heel (542.3 kg) was added to the fermenter and sterilized at 121° C. for 20 minutes. The water was cooled to 47° C. and the pretreated cob mixture was added through a feeder, situated on the top of the tank; 112.1 kg were added at this time. The pH was adjusted to 5.3 with 9.8 wt % $H_2SO_4$ and a first dose of enzymes was added. See Table 2 for the mass of the enzymes used and the corresponding dosages. Over the following nine hours, an additional 317.6 kg of pretreated corn cobs were added, with the pH controlled to 5.3 with 9.8 wt % $H_2SO_4$ throughout the additions. The target solids loading for this run was 25 wt %. At 12 hours after the first enzyme addition, a second dose was added (see Table 2). The fermenter was controlled at 47° C. and pH 5.3 for approximately 96 hours and the slurry was circulated through the recirculation loop. Starting at three hours after the first enzyme addition, a rotor-stator grinder in the recirculation loop was intermittently used to reduce the particle size of the pretreated cobs in the slurry. The grinder was used nine times for anywhere from 30 to 110 minutes at a time. At the end of the 96-hour run, some hydrolysate material was drawn off for use in these experiments. A sample of the hydrolysate was analyzed and the remainder was stored refrigerated until use. The results of the sample analysis are contained in Table 3.

TABLE 2

Enzymes used in MD07#3 saccharification

| Enzyme Name | Mass First Addition (kg) | Mass Second Addition (kg) | Overall Dosage (mg Protein/g glucan + xylan) |
|---|---|---|---|
| Spezyme ® CP | 3.72 | 14.77 | 16.6 |
| Multifect ® CX12L | 20.11 | 0.00 | 6.6 |
| Novozyme-188 | 0.75 | 2.92 | 4.2 |

TABLE 3

End of saccharification hydrolysate properties for MD07#3

| | |
|---|---|
| Monomer Glucose (g/L) | 72.50 |
| Oligomer Glucose (g/L) | 20.62 |
| Monomer Xylose (g/L) | 40.20 |
| Oligomer Xylose (g/L) | 43.74 |
| Monomer Arabinose (g/L) | 4.11 |
| Oligomer Arabinose (g/L) | 7.94 |
| Solids content (wt %) | 22.4% |

Clarified MD07#3 was produced from MD07#3 hydrolysate by centrifugation and filtration, with the final stage being filtration through a 0.2 µm filter.

Virginiamycin Sources

Lactrol® was purchased from Phibro (Ridgefield Park, N.J.) and is 100% virginiamycin.

Lactoside V™ and Lactoside 247™ were purchased from Lallemand Ethanol Technology (Milwaukee, Wis.).

Media

MRS=10 g/L peptone, 8 g/L meat extract, 4 g/L yeast extract, 20 g/L glucose, 5 g/L sodium acetate trihydrate, 1 g/L Tween 80, 2 g/L $K_2HPO_4$, 2 g/L triammonium citrate, 0.2 g/L $MgSO_4 \cdot 7H_2O$, 0.05 g/L $MnSO_4 \cdot 4H_2O$, pH 6.2.

HPLC Analysis

Fermentation samples were taken at timed intervals and analyzed for EtOH, residual sugars, and other metabolic products such as acetic acid, lactic acid, and glycerol using either a Waters HPLC system (Alliance system, Waters Corp., Milford, Mass.) or an Agilent 1100 Series LC; conditions=0.6 mL/min of 0.01 N H2SO4, injection volume=5 µL, autosampler temperature=10° C., column temperature=55° C., run time=25 min, detection by refractive index (maintained at 40° C.). The HPLC column was purchased from BioRad (Aminex HPX-87H, BioRad Inc., Hercules, Calif.). Analytes were quantified by refractive index detection and compared to known standards.

Example 1

Tolerance of Z. mobilis to Virginiamycin

Figure 2:
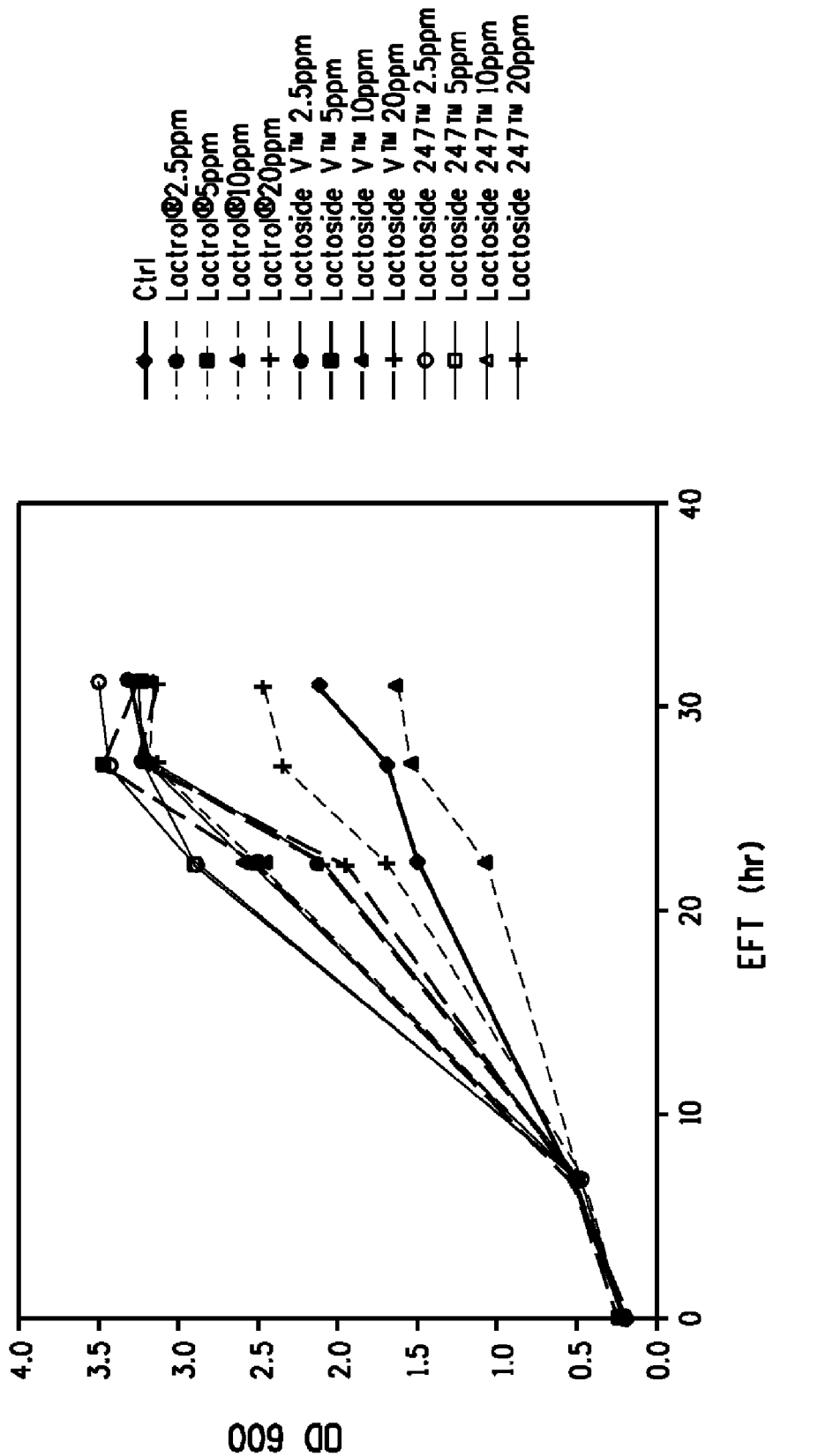
FIG. 2 is a graph showing growth of Z. mobilis strain ZW705 in clarified MD07#3 hydrolysate supplemented with 2 g/L yeast extract and Lactrol®, Lactoside V™, or Lactoside 247™ at different concentrations, and a control.

Z. mobilis strain ZW705 (described in General Methods) inoculum was prepared by reviving 2 mL of OD-10 frozen stock in MRM3G6 medium (10 g/L BBL yeast extract, 2 g/L $KH_2PO_4$, 1 g/L $MgSO_4*7H_2O$, 60 g/L glucose, pH 5.5) at 33° C. for ~8 hr. This culture was used to inoculate tubes containing clarified MD07#3 hydrolysate (see General Methods) supplemented with 2 g/L yeast extract and various virginiamycin preparations at a 20% (final volume) inoculation rate, producing an initial OD of ~0.5. Stocks of the virginiamycin-containing agents Lactrol®, Lactoside V™ or Lactoside 247™ were prepared at 1000 ppm in ethanol. These agents were added to the media at 2.5 ppm, 5 ppm, 10 ppm, or 20 ppm. The Lactrol® specifications indicate that the preparation is 100% activity, indicating that 2.5 ppm of Lactrol® is equivalent to 2.5 ppm of virginiamycin The initial ethanol concentration in each tube was brought to 1.94 vol % (200 µL in 10.3 mL) through addition of the virginiamycin-containing stocks and pure ethanol. The tubes were maintained at 33° C. with shaking for 32 hours, with growth monitored by measuring OD600. As shown in FIG. 2, ZW705 showed better growth in the presence of the virginiamycin-containing agents than for the control culture lacking virginiamycin, except in the 10 ppm Lactrol® medium.

Example 2

Effect of Virginiamycin on Controlling Contamination in Z. mobilis Seed Medium

Z. mobilis strain ZW705 (described in General Methods) inoculum was prepared by reviving 2 mL of OD-10 frozen stock in MRM3G6 medium (10 g/L BBL yeast extract, 2 g/L $KH_2PO_4$, 1 g/L $MgSO_4*7H_2O$, 60 g/L glucose, pH 5.5) at 33° C. for ~8 hr, at which point the OD was ~2. Lactobacillus plantarum strain ATCC 8014 inoculum was prepared by inoculating MRS medium with an individual colony and allowing growth at 33° C. for 8 hr, at which point the OD was ~0.4.

Figure 3A:
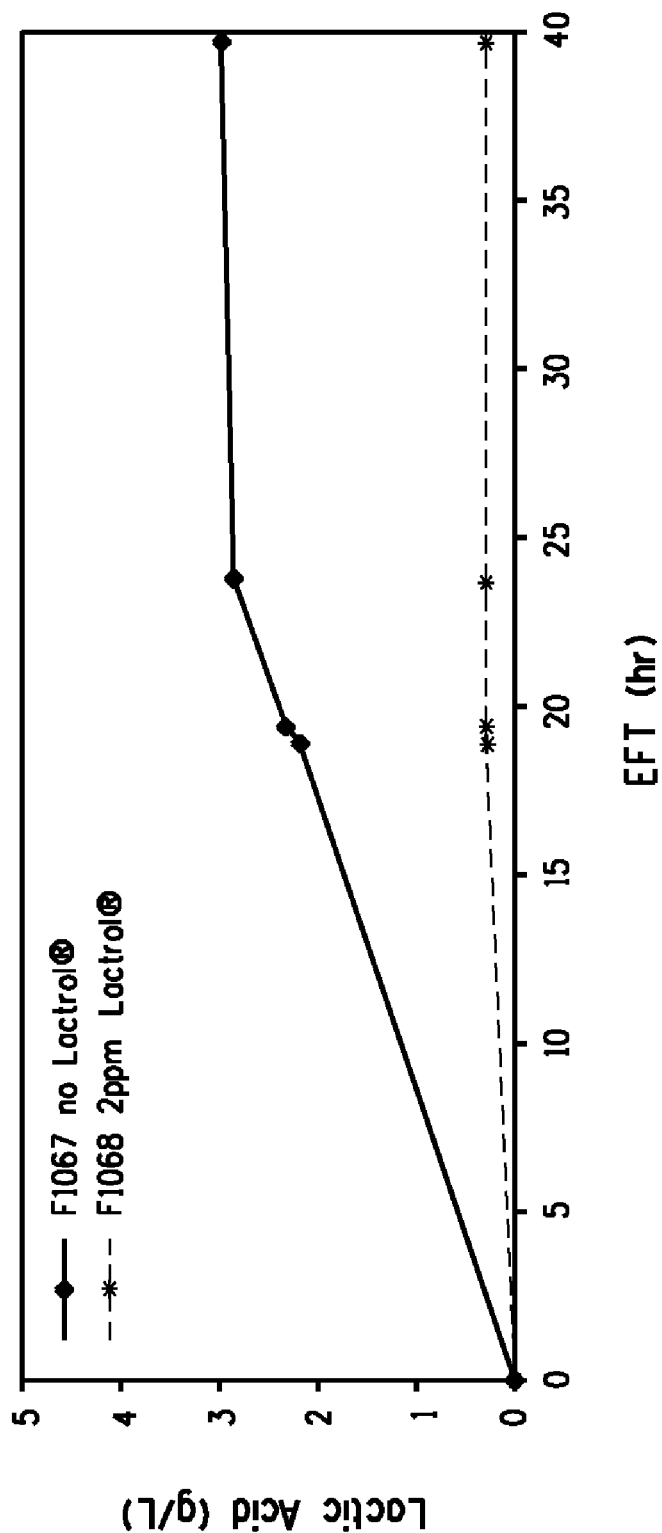
FIG. 3 shows graphs of lactic acid (A) or ethanol (B) concentration in cultures initially inoculated with a 1:100 ratio of Lactobacillus plantarum:Z. mobilis strain ZW705, in defined medium with (F1068) or without (F1067) 2 ppm of Lactrol®.
Figure 3B:
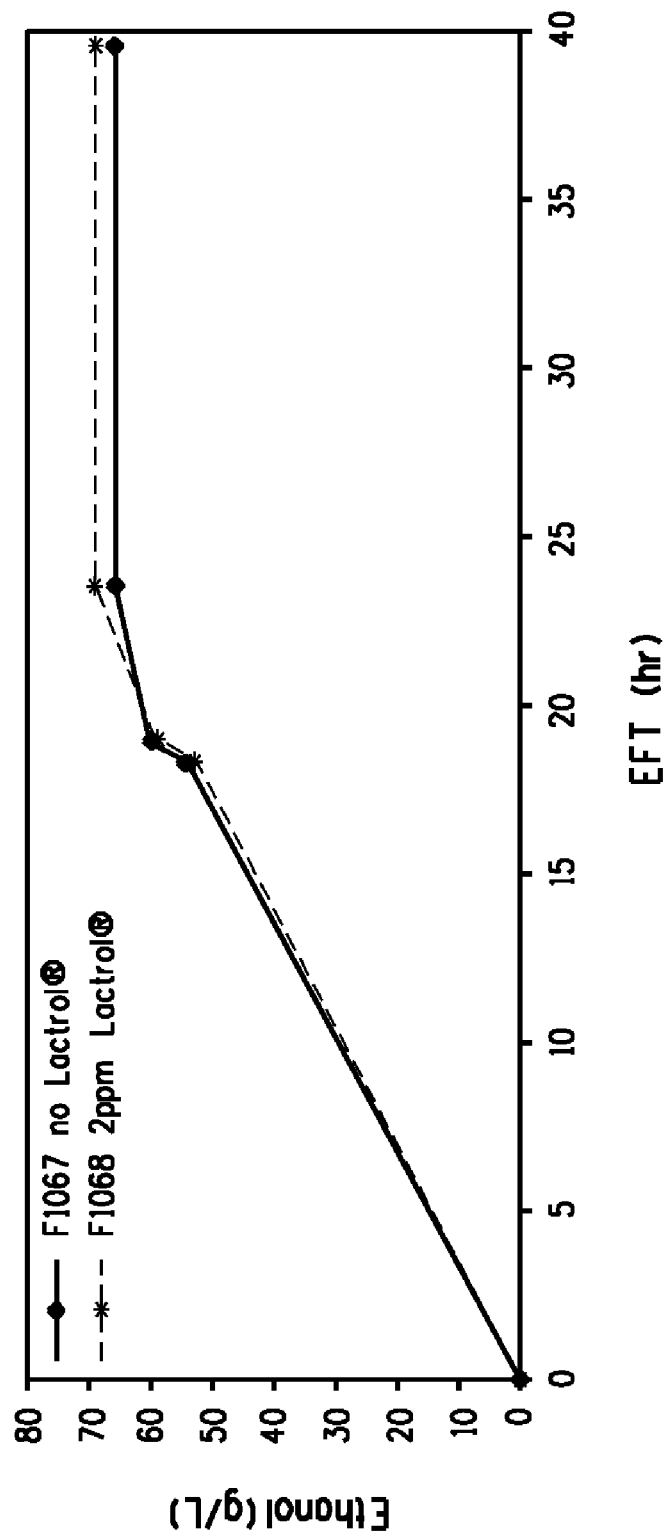

Seed medium (10 g/L Amberex695 yeast extract, 2 g/L $KH_2PO_4$, 5 g/L $MgSO_4*7H_2O$, 10 mM sorbitol, 150 g/L glucose, pH 5.5) was prepared and sterilized by autoclaving (121° C., 30 min). A sample of 500 mL of medium was inoculated with a mixture of Z. mobilis ZW705 (to OD of 0.05) and L. plantarum ATCC 8014 (to OD of 0.0005) producing a contamination level of 1:100, and fermented at 33° C. and pH 5.5 (4 N $NH_4OH$ added when needed for pH control). In a second sample, 2 ppm of Lactrol® was added. This is equivalent to 2 ppm of virginiamycin since Lactrol® is 100% active ingredient. The amounts of lactic acid and ethanol produced in the medium were assayed at different time points by HPLC (Aminex 87H column, 0.01 $NH_2SO_4$, 0.6 mL/min) and the results are shown in FIG. 3A (lactic acid) and 3B (ethanol).

In the absence of any antimicrobial (sample F1067), after 19.3 hr of fermentation, 2.4 g/L of lactic acid and 60.3 g/L of ethanol had formed. In the parallel culture with 2 ppm of Lactrol® added to the medium (sample F1068), 0.3 g/L of lactic acid was produced at 19.3 hr, illustrating the effectiveness of a 2 ppm Lactrol® dose in reducing L. plantarum growth, as evidenced by a reduced concentration of lactic acid. The amount of ethanol produced in the presence of Lactrol® remained equivalent to the amount produced in control culture.

Figure 4:
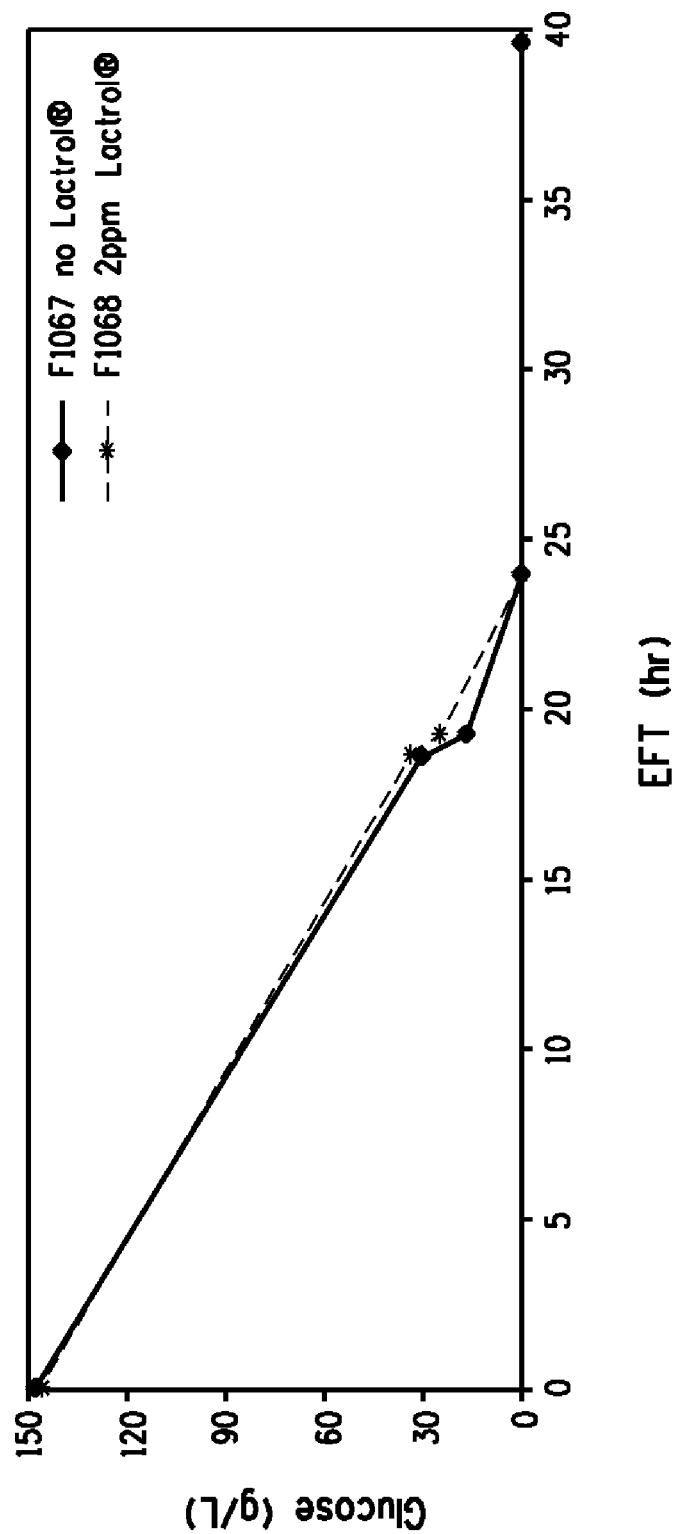
FIG. 4 shows a graph of glucose utilization in cultures initially inoculated with a 1:100 ratio of Lactobacillus plantarum:Z. mobilis strain ZW705, in defined medium with (F1068) or without (F1067) 2 ppm of Lactrol®.

Glucose was also measured by HPLC, as described above, and results showed that glucose consumption was similar for the cultures with and without Lactrol® (FIG. 4).

Example 3

Figure 5A:
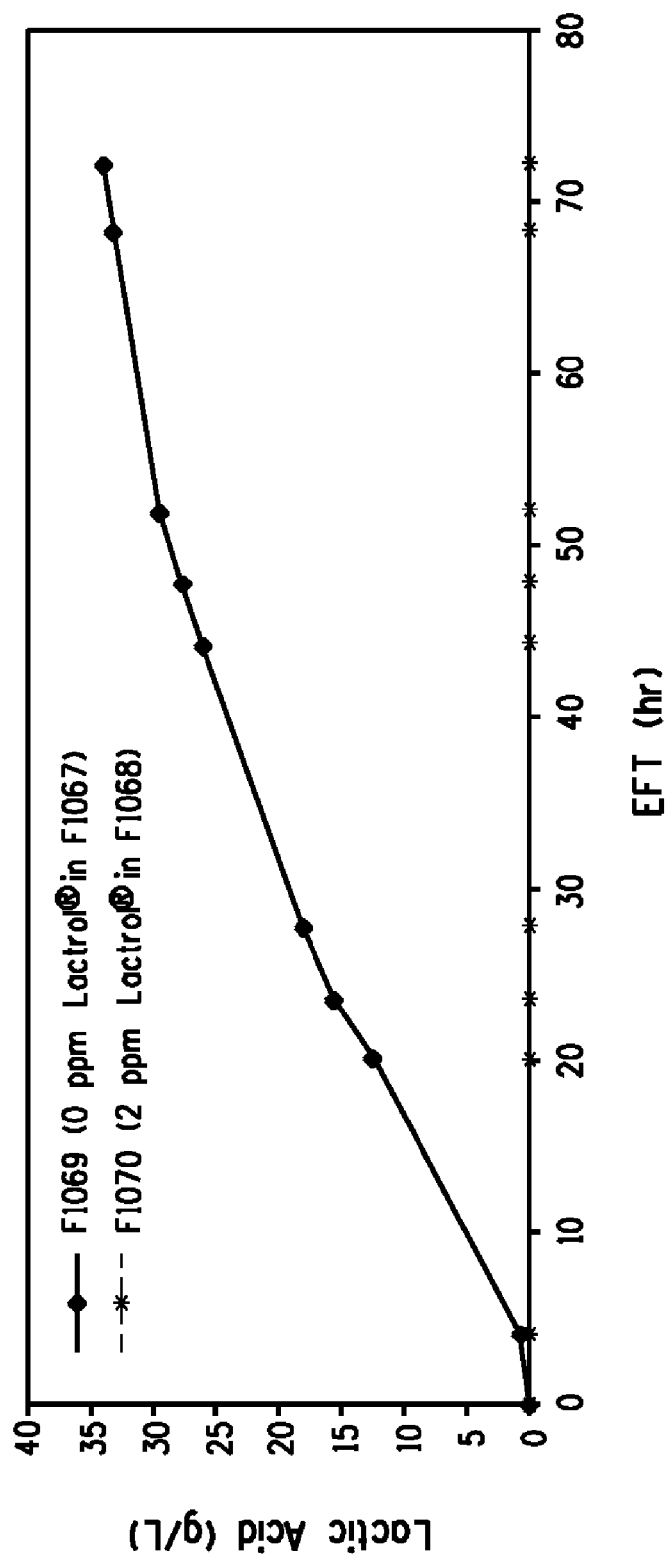
FIG. 5 shows graphs of lactic acid (A) or ethanol (B) concentration in hydrolysate medium inoculated with a seed culture initially contaminated with a 1:100 ratio of L. plantarum:Z. mobilis strain ZW705 and grown in medium lacking virginiamycin (F1069) or grown in medium containing 2 ppm of Lactrol® (F1070).
Figure 5B:
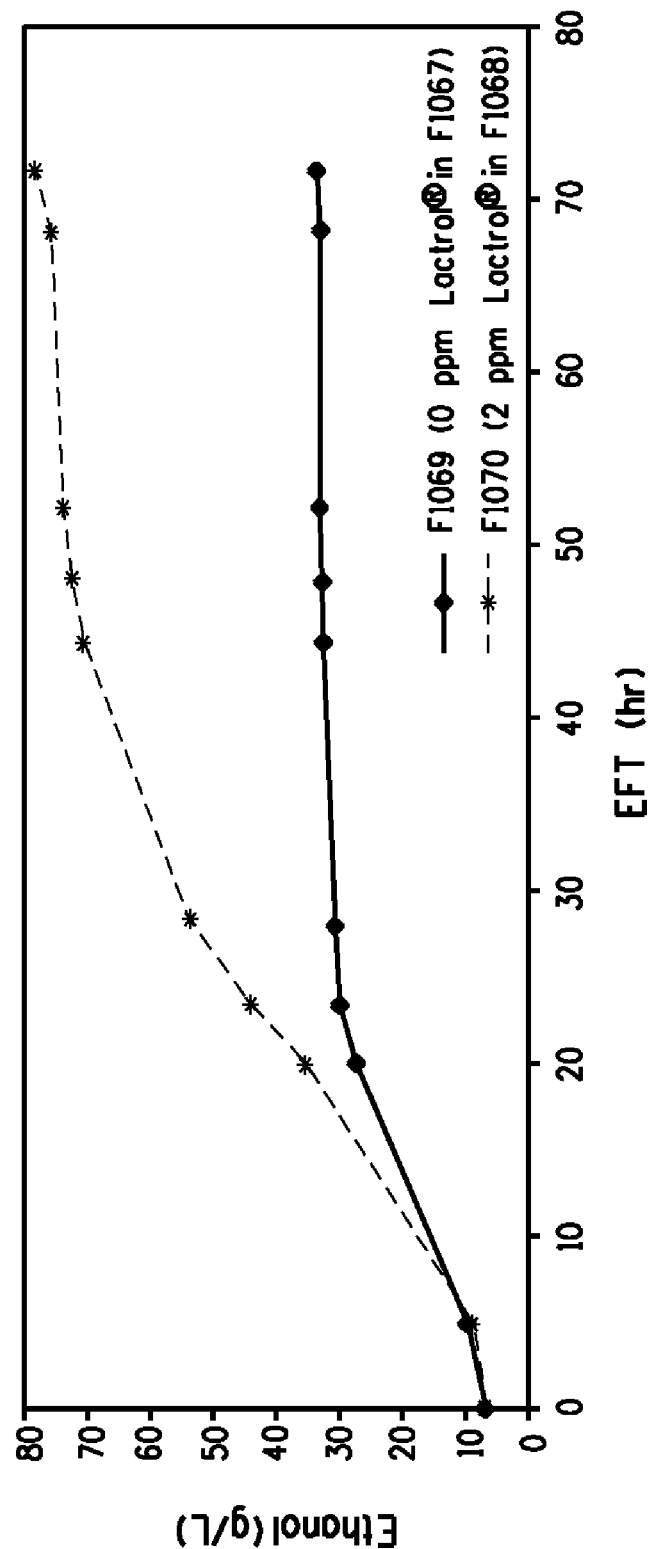

Effect of Using Virginiamycin-Treated Z. mobilis Seed as Hydrolysate Medium Inoculum A sample of the F1067 culture (no Lactrol®) at EFT=19.3 hr from Example 1 was used as a seed culture to inoculate 450 mL of cob hydrolysate medium (FRF13; see General Methods) (adjusted to pH 5.8, +10 mM sorbitol) at 10 vol % (final volume), which was fermented at 33° C. (reduced to 30° C. at EFT=21 hr) and pH 5.8 (adjusted with 4 N NaOH). After 48 hr of fermentation (sample F1069), 27.6 g/L of lactic acid (FIG. 5A) and 32.6 g/L of ethanol (FIG. 5B) had formed. In a parallel experiment a sample of the F1068 culture (with 2 ppm Lactrol®) at 19.3 hr (from Example 1) was used as the seed culture for inoculating the same medium at the same 10 vol %. After 48 hr of fermentation (sample F1070), 73.5 g/L of ethanol had formed (FIG. 5B), with no detectable lactic acid produced (FIG. 5A). The results showed that a small dose of Lactrol® used in the contaminated seed was sufficient to prevent contamination of hydrolysate fermentation.

Figure 6A:
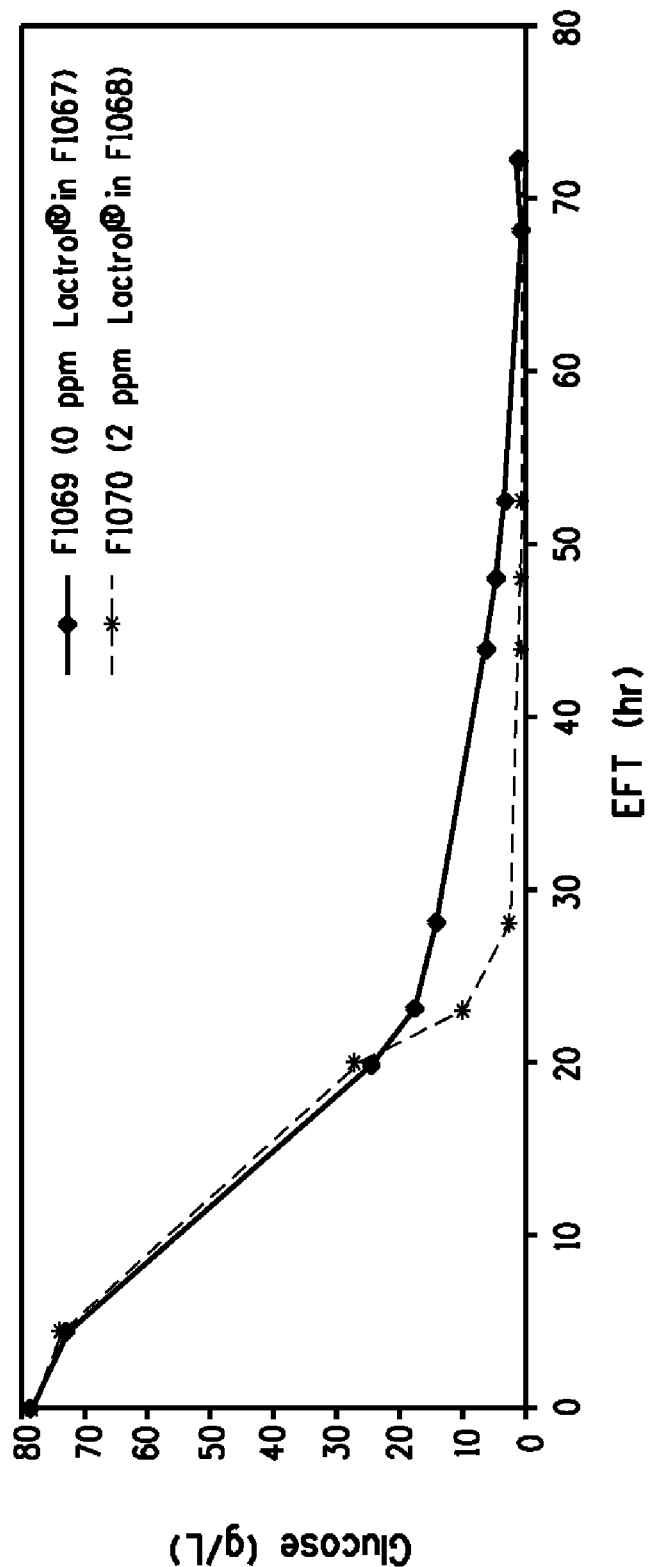
FIG. 6 shows graphs of glucose (A) and xylose (B) utilization in hydrolysate medium inoculated with a seed culture initially contaminated with a 1:100 ratio of L. plantarum:Z. mobilis strain ZW705 and grown in medium lacking virginiamycin (F1069) or grown in medium containing 2 ppm of Lactrol® (F1070).
Figure 6B:
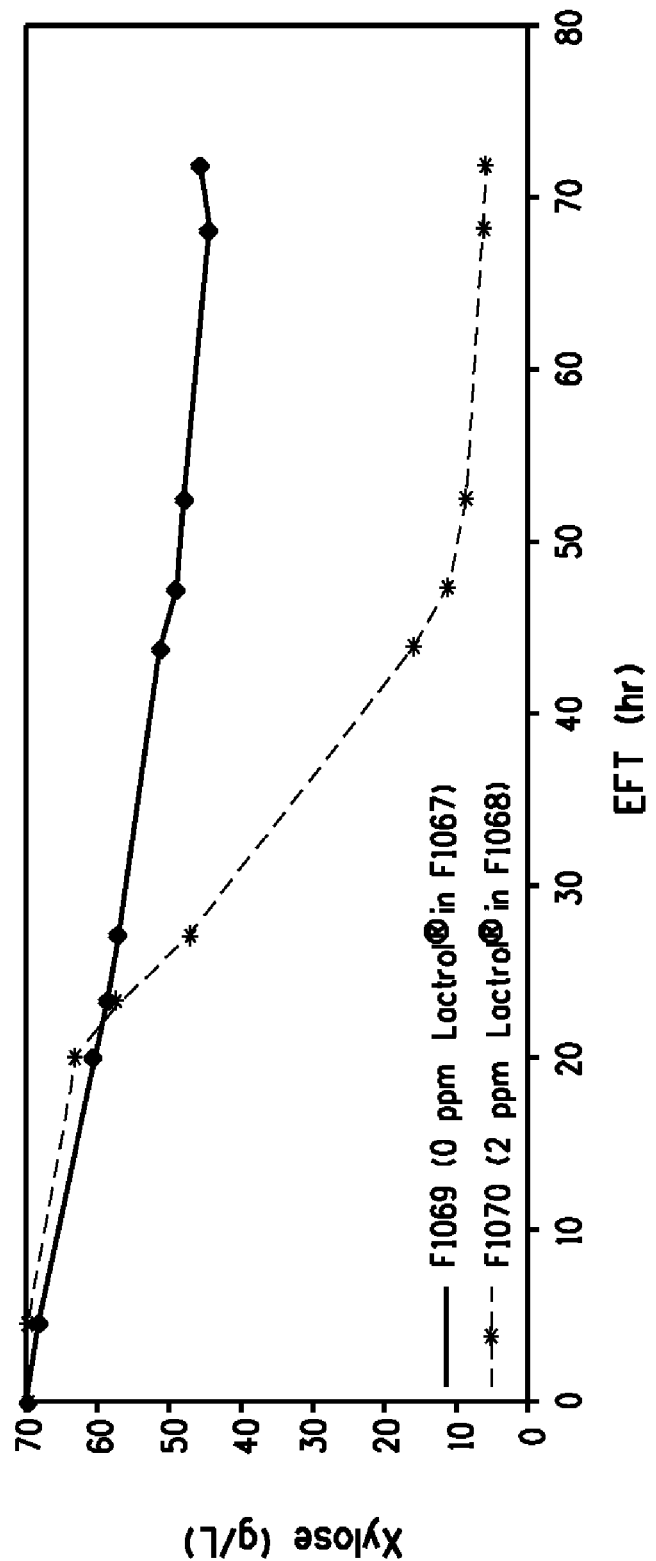

Xylose and glucose were also assayed during both hydrolysate fermentations by HPLC as described above, and the results are shown in FIG. 6. Both fermentations showed complete glucose consumption, however the fermentation inoculated with the Lactrol®-containing seed consumed glucose more rapidly. The fermentation inoculated with the Lactrol®-containing seed also had almost complete xylose consumption, while over 50% of xylose was not consumed in the fermentation inoculated with seed lacking Lactrol® (FIG. 6).

Example 4

Effect of Virginiamycin on Contaminated Z. mobilis Hydrolysate Fermentation

To determine the Lactrol® dose required to prevent lactic acid formation during hydrolysate fermentation, a portion of intentionally-contaminated seed culture F1067 at EFT=19.3 hr (from Example 1) was used as a seed culture to inoculate cob hydrolysate medium (FRF13; see General Methods) (adjusted to pH 5.8, +10 mM sorbitol) at 10 vol % (final volume) containing either 0 ppm (sample F1069) or 2 ppm (sample F1071) of Lactrol®, which was then fermented at 33° C. (reduced to 30° C. at EFT=21 hr) and pH 5.8 (adjusted with 4 N NaOH).

Figure 7A:
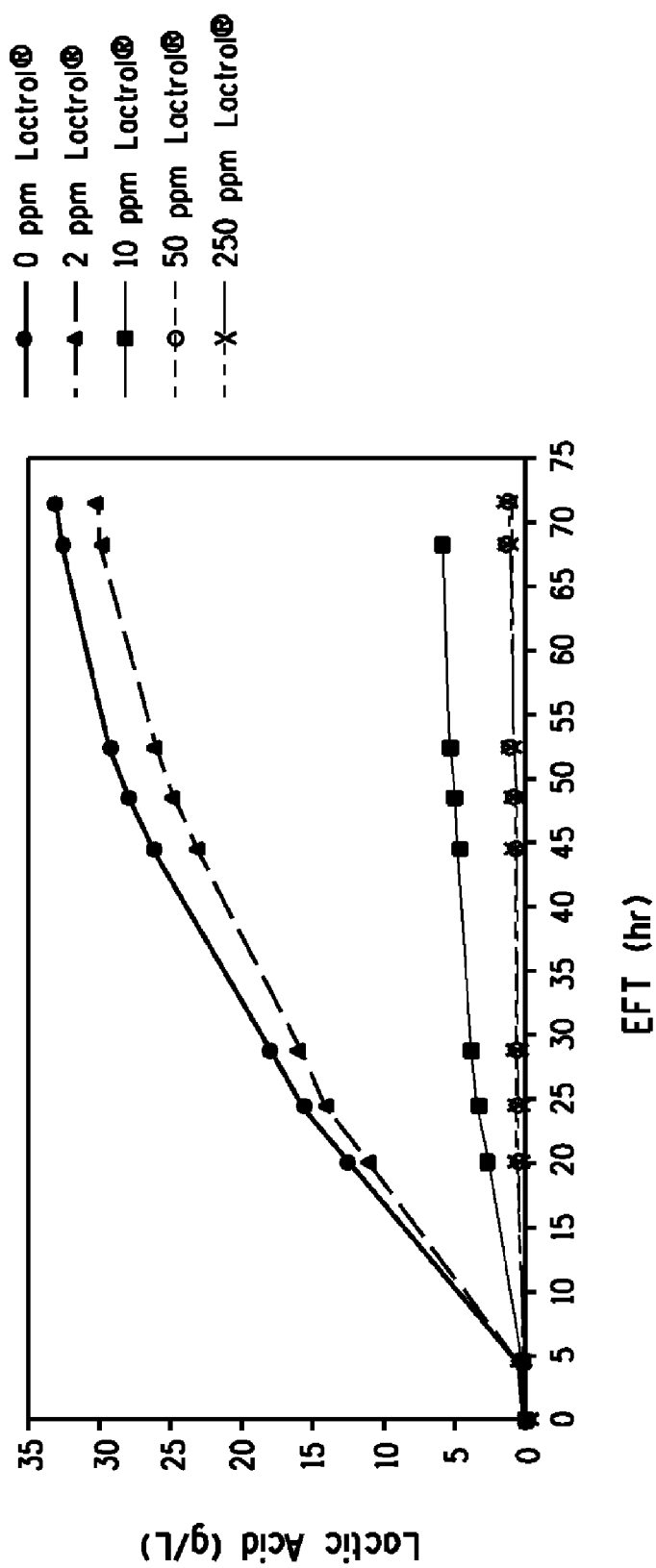
FIG. 7 shows graphs of lactic acid (A) or ethanol (B) concentration in cultures grown in hydrolysate medium containing different concentrations of Lactrol®, that were inoculated with a seed culture initially contaminated with a 1:100 ratio of L. plantarum:Z. mobilis strain ZW705 and grown without virginiamycin.

To explore higher concentrations of Lactrol®, a seed culture similar to F1067 was produced and used as inoculum for cob hydrolysate fermentation in a similar manner to that described above, in the presence of 10, 50, or 250 ppm Lactrol® (samples F1081-1083, respectively). The results in FIG. 7A show that after 45 hours large quantities (>20 g/L) of lactic acid were produced in medium containing 0 and 2 ppm Lactrol®. Including 10 ppm Lactrol® reduced lactic acid formation to ~5 g/L at 45 hours. Including 50 and 250 ppm Lactrol® maintained lactic acid concentration at <1 g/L, illustrating the need for higher concentrations of virginiamycin for control of contaminating microorganisms during hydrolysate fermentation.

Figure 7B:
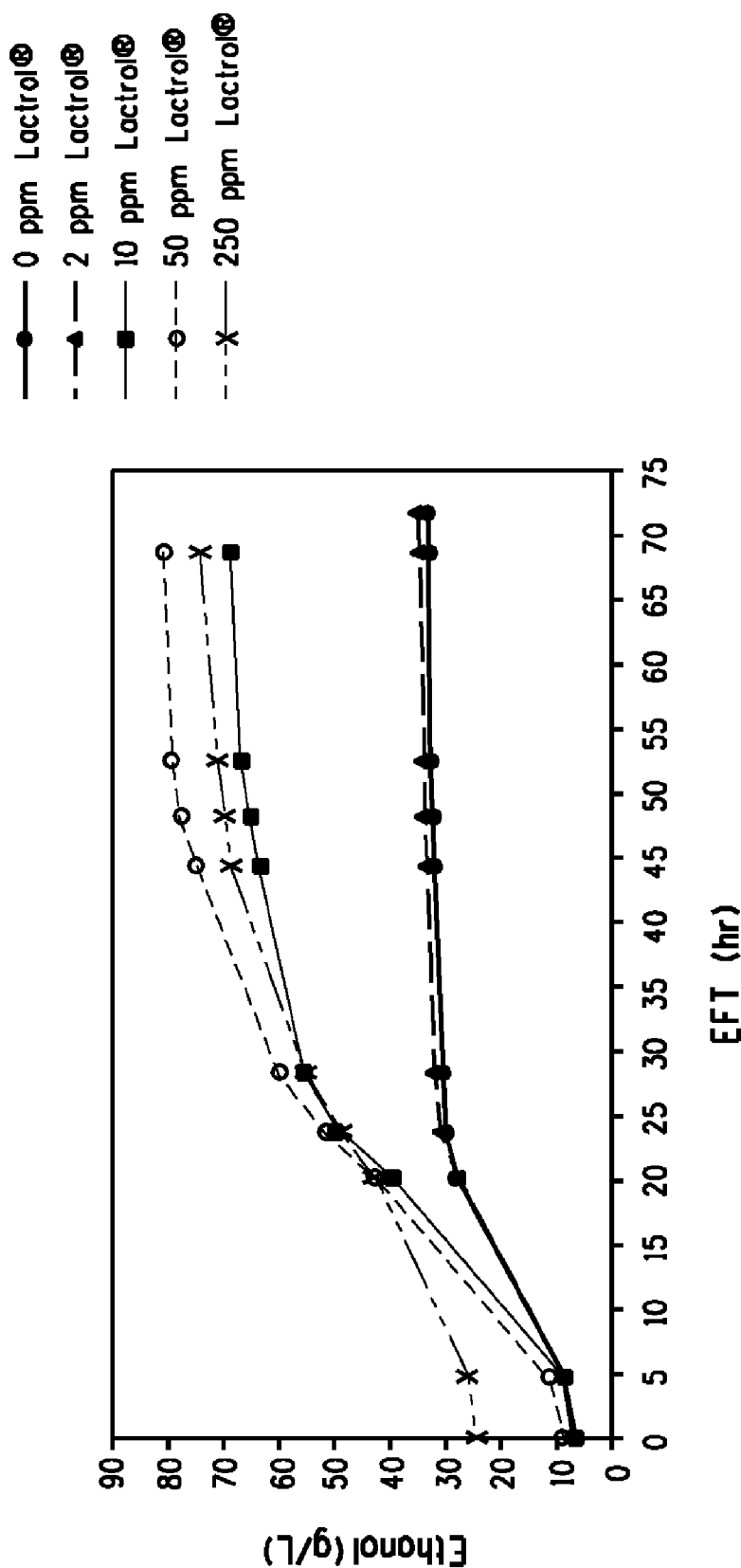

Ethanol production was greater in fermentations containing 10 ppm, 50 ppm, or 250 ppm of Lactrol® than in fermentations containing 0 ppm or 2 ppm, as shown in FIG. 7B.

What is claimed is:

1. A method for controlling bacterial contamination in a fermentation using a *Zymomonas* cell biocatalyst comprising:
   a) providing a fermentation medium;
   b) adding virginiamycin to the fermentation medium to a concentration of at least about 10 ppm;
   c) adding to the fermentation medium an inoculum of *Zymomonas* cells, thereby producing a fermentation broth; and
   d) maintaining the fermentation broth under conditions suitable for growth of the *Zymomonas* cells;
wherein steps b) and c) may be performed in either order or concurrently and wherein bacterial contamination is controlled.

2. The method of claim 1 wherein the *Zymomonas* cells produce ethanol in the fermentation broth.

3. The method of claim 1 or 2 wherein the fermentation medium lacks cellulosic biomass hydrolysate.

4. The method of claim 1 or 2 wherein the fermentation medium comprises cellulosic biomass hydrolysate.

5. A method for producing ethanol comprising:
   a) providing a fermentation medium;
   b) adding to the fermentation medium an inoculum of *Zymomonas* cells grown in the presence of virginiamycin, producing a fermentation broth, wherein the concentration of virginiamycin is at least about 10 ppm; and
   c) maintaining the fermentation broth under conditions suitable for growth of the *Zymomonas* cells and production of ethanol by the *Zymomonas* cells;
   wherein no virginiamycin is added to the fermentation medium separately from the inoculum of (b) and wherein ethanol is produced.

6. The method of claim 5 wherein the fermentation medium comprises cellulosic biomass hydrolysate or lacks cellulosic biomass hydrolysate.

7. A method for improving growth of *Zymomonas* cells comprising growing *Zymomonas* cells in fermentation medium comprising virginiamycin wherein the concentration of virginiamycin is at least about 10 ppm.

* * * * *